United States Patent [19]
Wysor et al.

[11] Patent Number: 4,532,122
[45] Date of Patent: Jul. 30, 1985

[54] ANTI-TRYPANOSOMAL ACTIVITY OF PLATINUM CO-ORDINATION COMPOUNDS

[75] Inventors: Michael S. Wysor, Hyattsville; Leonard A. Zwelling, Potomac, both of Md.

[73] Assignee: The United States of America as represented by the Secretary of the Army, Washington, D.C.

[21] Appl. No.: 250,991

[22] Filed: Apr. 3, 1981

[51] Int. Cl.$^3$ .............................................. A61K 33/24
[52] U.S. Cl. ...................................... 424/10; 424/131
[58] Field of Search ................................... 424/131, 10

[56] References Cited

PUBLICATIONS

Borch et al., Proc. Natl. Acad. Sci., USA, vol. 76, No. 12, pp. 6611–6614, (Dec. 1979).
Kinnamon et al., Antimicrobial Agents and Chemotherapy, Feb. 1979, pp. 157–160.

Primary Examiner—Jerome D. Goldberg
Attorney, Agent, or Firm—William G. Gapcynski; Jack M. Petruncio; Werten F. W. Bellamy

[57] ABSTRACT

A novel method has been developed for improved chemotherapy of animals infected with African trypanosomiasis. The method involves the concurrent administration of therapeutically effective amounts of cis-diamminedichloroplatinum (II) and bis-(diethylthiocarbamoyl)disulfide (disulfiram) or diethyl dithiocarbamate to the hydrated animal.

4 Claims, No Drawings

ANTI-TRYPANOSOMAL ACTIVITY OF PLATINUM CO-ORDINATION COMPOUNDS

DECLARATION CLAUSE

The invention described herein may be manufactured, used and licensed by or for the Government for governmental purposes without the payment to us of royalties thereon.

BACKGROUND OF THE INVENTION

This invention relates to a novel method for treating African trypanosomiasis, a disease complex resulting from infection of a mammalian host by certain pathogenic protozoa known as trypanosomes. When African trypanosomiasis occurs in man, the untreated disease proceeds to fatal termination with the victim in the comatose state commonly referred to as sleeping sickness. This invention centers upon achieving reliable and safe treatment of African trypanosomiasis with cisplatin [cis-diamminedichloroplatinum (II)] and disulfiram (bis(diethylthiocarbamoyl)disulfide) or diethyl dithiocarbamate to ameliorate the toxic effects of cisplatin.

African sleeping sickness is a disease endemic on the African continent and some adjacent islands. On occasion, great epidemics of this severe, progressive disease have arisen, resulting in extremely high fatality rates among those victims not treated with trypanocidal drugs. The disease in man is caused by either of two protozoan parasites, *Trypanosoma gambiense* or *Trypanosoma rhodesiense*, which are transmitted by the bite of an infected fly of the genus Glossina (usually called tsetse flies). Infections caused by the former parasite usually run a more chronic course than those involving *Trypanosoma rhodesiense*. The former generally occurs to the west of the Rift Valley in Africa and has been called Gambian sleeping sickness. The latter infection predominates to the east of the Rift Valley and is known as Rhodesian sleeping sickness. These devastating diseases have had continuing and drastic effects upon tropical Africa. Not only has man succumbed in great legions to those trypanosomiases but also allied trypanosomes transmitted by infected tsetse flies have rendered some 2,000,000 square miles of that continent inhospitable for man's animals. Thus, the protein malnutrition of tropical Africa has been traced in part to the partial vegetarianism enforced on a society in which it is impossible to raise common domestic animals owing to diverse trypanosome infections of these animals.

Although partially effective drugs are available for therapy and prophylaxis, all presently employed drugs have very serious, toxic side effects. Less toxic and effective chemical treatment procedures are needed urgently.

Presently, progress toward control of the trypanosomiases has been relatively minor. Attempts to achieve eradication or control of the insect vector have failed. No adequate vaccine is available. Chemotherapy has involved use of agents highly toxic to the host, and chemoprophylaxis has been fraught with many hazards at low levels of effectiveness. Drugs available for treatment of early infections in man have remained the same for some twenty years, and no new agents have been introduced in more than 30 years for treating late-stage trypanosomiasis. Less toxic, more effective trypanocides remain an urgent need in tropical medicine and in tropical public health especially in Africa.

SUMMARY OF THE INVENTION

Laboratory animals of diverse sorts have been employed in studies with trypanosomes. From the standpoint of chemotherapeutic investigations, infections produced by the Wellcome CT strain of *Trypanosoma rhodesiense* to ICR/Ha Swiss mice have proven to be reliable laboratory models for trials of candidate drugs. This method has been reported in detail: L. Rane, D. S. Rane, and K. E. Kinnamon, Am. J. Trop. Med. Hyg., 25, 395-400 (1976).

In the approach to development of new and more effective trypanocides using the above-mentioned model infection, numerous chemical types having diverse biological effects have been selected for testing. One such probing involved the study of numerous antitumor agents known to exert efforts through diverse mechanisms: K. E. Kinnamon, E. A. Steck, and D. S. Rane, Antimicrobial Agents and Chemotheraphy, 15, 157-160 (1979). In that report, cisplatin [there identified as cis-diamminedichloroplatinum (II)] was found to have anti-trypanosomal effects at dose levels which were unsuitably toxic to the test animals. In fact, by repetition of the testing using an aqueous vehicle instead of the peanut oil in the method of Rane, et al (loc. cit.) as reported by Kinnamon, et al (loc. cit.), toxicity of cispilatin overwhelmed the infected mice at doses requisite for anti-trypanosomal effects.

This invention relates to a method for alleviating the toxicity of cisplatin while retaining its effectiveness against *Trypanosoma rhodesiense*. The novel finding lies in the fact that concurrent treatment of hydrated, trypanosome-infected mice with cisplatin and disulfiram or diethyl dithiocarbamate effected cures of the infection with very good survival and little damage to test animals. In essence, oral disulfiram protected the kidneys and gastrointestinal tracts from the toxic effects of the anti-trypanosomal drug, without compromising its chemotherapeutic activity.

DETAILED DESCRIPTION OF THE INVENTION

The considerable and complex nature of problems in various developing countries of tropical Africa have been worsened by the increasing incidents of trypanosomiasis. Drugs for the management of this highly fatal infection have been generally inadequate or/and highly toxic to the victim. The present invention relates to a novel means for alleviating the toxic effects of an agent useful in the treatment of highly fatal trypanosome infections in animals. It has been established that trypanocidally effective doses of cisplatin are markedly toxic when administered to mice infected with *Trypanosoma brucei rhodesiense*. However, cures have been achieved safely by concurrent hydration of the animals and oral dosing with disulfiram. This procedure was firmly established as affording parasitologic cures of the experimental animals by subinoculation of tissues (blood, brain, heart) into recipient mice from mice cured of trypanosomiasis in accordance with the method of this invention. These tissues did not produce the trypanosomiasis in the recipient mice.

The novel method of this invention provides an effective means for ready application to man. In particular, cisplatin has found noteworthy place in the chemotherapy of diverse malignancies in man, and disulfiram is widely used in the management of alcoholism. Moreover, the drugs are presently available, thus not requiring either detailed assessment of profiles in clinical pharmacology nor detailed investigation of chemical art required for their production and pharmaceutical specifications.

Giving to the well-known clinical use of cisplatin in treatment of malignancies, application of the newly developed "rescue" technique by ameliorating its toxic effects by concurrent administration of disulfiram could also be of significant value in cancer chemotheraphy.

EXPERIMENTAL

Examples herein offered to illustrate this invention are not intended to delimit the scope thereof regarding amelioration of the toxic effects of cis-diamminedichloroplatinum (II) by concurrent dosing with bis-(diethylthiocarbamoyl) disulfide. Rather, the profile of experiments has been chosen to afford basis for the safe and satisfactory use of the drugs for curing animals infected with African trypanosomes. Prior to the discovery by applicants of the subject invention, anti-trypanosomal activity of cisplatin could not be used at safe and effective doses due to its toxicity. Surprisingly, the use of applicants' inventive method has made it possible to cure animals of trypanosomiasis without the characteristic toxic hazards associated with chemotherapeutic agents.

MATERIALS

Cisplatin drug [chemically known as cis-diamminedichloroplatinum (II) and identified as NSC 119873 by the National Cancer Institute of the U.S.A.] was used as the clinical formulation, obtained from the Drug Synthesis and Chemistry Branch of the National Cancer Institute. Each 10 ml vial contained an aqueous solution of 10 mg cisplatin, 100 mg mannitol, and 90 mg sodium chloride. Disulfiram [chemically, bis-(diethylthiocarbamoyl) disulfide] was pharmaceutical grade product obtained from Ayerst Laboratories, New York. It was dissolved in a 1:4 v/v mixture of normal saline solution-glycerol for oral administration of disulfiram.

METHODS

Animal Testing

Anti-trypanosomal activity reported in this invention was determined according to the procedure outlined in the article of L. Rane, et al entitled "Screening Large Numbers of Compounds in a Model Based on Mortality of *Trypanosoma rhodesiense* Infected Mice," The American Journal of Tropical Medicine and Hygiene, Volume 25, No. 3, pages 395–400 (1966). To summarize, however, experiments were conducted with the Wellcome CT strain of *Trypanosoma rhodesiense* originally isolated in 1934. The test system is patterned after the one developed and employed in testing of compounds for activity against *Plasmodium berghei* malaria [see Osdene, et al, New Series of Potential Antimalarial Agents, J. Med. Chem., 10, 431–434 (1967)]. The test system is based on comparisons of responses to test compounds by ICR/HA Swiss mice infected with the strain as expressed in mean survival times compared with mean survival times of untreated controls.

By using a standard inoculum of $1 \times 10^6$ trypanosomes, it was possible to produce a uniform disease fatal to 100% of untreated animals within four to six days, with a mean survival time of $4.45 \pm 0.24$ days. Test mice (of similar age were females and 21 to 25 grams in weight) received an intraperitoneal injection of 0.5 ml of a 1:50,000 dilution of heparinized heart blood drawn from donor mice infected with *Trypanosoma rhodesiense* 3 days earlier.

Deaths prior to the fourth day (when untreated controls begin to die) were regarded as not related to the infection and were scored as "toxic deaths." Treated animals were kept under observation for 30 days. Parasitemias were monitored by thick blood film smears (taken from tail veins of the mice) every 2 days for the 30-day course of the experiment. Survivors at the end of 30 days were considered cured. An increase of 100% in mean survival time over control animals was considered as a minimum effective response. In calculating mean survival times, toxic deaths and 30 day survivors were not included.

Histopathology

Owing to the fact that cisplatin has well-known, dose-limiting nephrotoxic effects, manipulations which would ameliorate acute toxicity might not prevent cumulative, chronic renal damage. Thus, histopathologic studies were requisite.

Mice were divided into three groups for serial sacrifices: (a) trypanosome-infected mice treated with cisplatin, saline hydration and disulfiram (15 mice/group); (b) uninfected mice similarly treated (15 mice/group); and (c) infected mice, treated with cisplatin without hydration or disulfiram (5 mice/group). Two mice from each of these groups were necropsied at various times following cisplatin treatment. Mice for autopsy examination were sacrificed by $CO_2$ inhalation 8, 10, 15, 18, 22, 25 or 32 days following the initiation of cisplatin treatment. Tissues were fixed in 10% neutral buffered formalin, imbedded in paraffin, sectioned to 6–8$\mu$ and stained with hematoxylin and eosin.

EXAMPLES

Examples 1 through 3—Effects of Cisplatin on Uninfected Mice

Cisplatin was injected intraperitoneally into healthy mice at 3 mg/kg per day for 5, 6, or 7 days. Ten animals were used in each of three test procedures for the three regimens of drug dosing. The test procedures included: no hydration of mice; hydration of mice; and hydration plus disulfiram administration to the animals. Hydration was achieved by subcutaneous administration of 3 ml of normal saline solution every 6 hours for the duration of cisplatin administration. Oral dosing with disulfiram was done by giving 250 mg/kg of the drug exactly 4 hours following each dose of cisplatin. Table 1 provides summary of data resulting from these studies showing 30-day survival as an indication of the effects of cisplatin on uninfected mice.

From the tabulation, it is evident that cisplatin gave no evidence of delayed toxic effects when 3 mg/kg of drug were administered daily for 5 days; however, more prolonged dosing did cause significant toxic damages. Mortality from cisplatin administration was ameliorated by hydration, with or without use of disulfiram.

Renal lesions were highly common among mice treated with cisplatin, alone, and subjected to histopathologic study (two mice per group). Early lesions consisted of acute proximal and distal tubular necrosis. In mice necropsied on day 18 or later, the renal cortex contained multifocal accumulations of lymphoplasmacytic inflammatory cells with areas of tubular regeneration. In addition to renal lesions, colonic and jejunal enteritis, and interstitial pneumonia with edema and vascular congestion were also seen.

TABLE 1

30-Day Survival of Mice Treated with Cisplatin

| Example | No. of Days of Therapy | No Hydration % | With Hydration % | Hydration + Disulfiram % |
|---|---|---|---|---|
| 1 | 5 | 100 | | |
| 2 | 6 | 10 | 100 | 100 |
| 3 | 7 | 0 | 90 | 100[a] |

All groups included 10 mice except where indicated. Therapy was 3 mg/kg bodyweight per day of cisplatin given intraperitoneally for number of days indicated. Disulfiram (250 mg/kg-orally) was given exactly four hours following each cisplatin dose. Hydration was 3 ml of physiologic saline given subcutaneously four times per day. Survival is given as % survival 30 days following initial therapy.
[a]Average survival from four experiments with 10 mice per experiment.

Examples 4 through 6—Effects of Cisplatin on Mice Infected with Trypanosomes Mice were infected with *Trypanosoma rhodesiense* as described and 30 minutes thereafter, therapy with cisplatin was initiated. The therapeutic regimen was that described in Examples 1 through 3. Table 2 (i.e., Examples 4 through 6) provides a summary of the effects of cisplatin alone, with hydration, and with hydration plus disulfiram upon 30-day survival of trypanosome-infected mice.

It is to be seen that five-day therapy with cisplatin, alone, gave poor survival among infected mice. In fact, it was shown that such course of treatment failed to clear the bloodstream of trypanosomes. Six daily doses of cisplatin, alone or with hydration, gave no survivors after 30 days, while addition of disulfiram to the regimen provided for survival of 62.5% of infected mice so treated. This later was not evidence of a dependable cure among the mice, for, although the blood was temporarily cleared of trypanosomes, relapses of parasitemia occurred. Some animals suffered relapses 6 to 14 days after the last doses. On the other hand, the 7-day regimens (cisplatin with hydration and, with hydration plus disulfiram) were effective in curing mice of the *Trypanosoma rhodesiense* infections. When 3 mg/kg of cisplatin was administered daily for seven days, with hydration plus disulfiram, there resulted the greatest number of long-term survivors. That was consequent to marked reduction in the toxicity of cisplatin. The regimen was shown to be fully curative, and not merely palliative. All survivors at 30 days were sacrificed, and tissues (blood; heart; brain) subinoculated into healthy mice. No recipient mice developed trypanosome infection. Thus, no latent trypanosomes had survived the therapy. Disulfiram, alone, was shown to lack antitrypanosomal activity in the model test system.

Prior work [Kinnamon, et al, loc. cit.] had demonstrated that cisplatin exhibited anti-trypanosomal effects at toxic dose levels. In this investigation, it has been confirmed that cisplatin does exert curative effects on *Trypanosoma rhodesiense* infections in mice, however, the large doses required (3 mg/kg/day for 7 days) made the drug, itself, extremely hazardous. This invention relates to a novel means for alleviating the toxicity of cisplatin by concurrent administration in a regimen involving hydration and disulfiram, while eradicating infections with *Trypanosoma rhodesiense* through lethal effects upon parasites in the blood and bound in tissues. In a few instances (Table 2), the treatment either failed to cure the animals, or relapse occurred. It is probable that further dose-ranging work will establish an optimal course of treatment based upon findings fundamental to this invention.

TABLE 2

30-Day Survival of Trypanosome-Infected Mice Treat with Cisplatin

| Example | No. of Days of Therapy | No Hydration % | WITH TRYPANOSOMES With Hydration % | Hydration + Disulfiram % |
|---|---|---|---|---|
| 4 | 5 | 10 | | |
| 5 | 6 | 0 | 0[a,b] | 62.5[a,b,c] |
| 6 | 7 | 0[a] | 57[a] | 92.5[c] |

All groups included 10 mice except where indicated. Therapy was 3 mg/kg bodyweight per day of cisplatin given 30 minutes after infection with trypanosomes and subsequently given intraperitoneally for number of days indicated in first column. Disulfiram (250 mg/kg-orally) was given exactly four hours following each cisplatin dose. Hydration was 3 ml of physiologic saline given subcutaneously four times per day. Survival is given as % survival 30 days following initial therapy.
[a]Blood of all mice was cleared of trypanosones.
[b]Relapse of parasitemia.
[c]Average survival from four experiments with 10 mice per experiment.

We claim:

1. A method for treating an animal infected with African trypanosomiasis for seven consecutive days consisting of the steps of administering to said animal a therapeutically effective amount of chemical agents consisting of (a) intraperitoneal administration of 3 mg/kg bodyweight of an aqueous solution of cis-diamminedichloroplatinum (II) once a day; (b) subcutaneous administration of 3 ml of physiologic saline four times a day at six hour intervals to maintain hydration; and (c) oral administration of 250 mg/kg bodyweight of disulfiram or parenteral administration of 250 mg/kg bodyweight of diethyl dithiocarbamate four hours after step (a), once a day.

2. The method of claim 1 wherein the African trypanosomiasis being treated is caused by *Trypanosoma rhodesiense*.

3. The method of claim 1 wherein the aqueous solution in step (a) consists of mannitol and sodium chloride.

4. The method of claim 3 wherein the chemical agent of step (a) consists of 10 mg of cis-diamminedichloroplatinum (II), 100 mg of mannitol and 90 mg of sodium chloride.

* * * * *